United States Patent [19]

Hall et al.

[11] Patent Number: 4,575,512
[45] Date of Patent: Mar. 11, 1986

[54] 7-OXABICYCLOHEPTANE SUBSTITUTED OXA PROSTAGLANDIN ANALOGS AND THEIR ANTI-THROMBOTIC COMPOSITIONS AND METHODS

[75] Inventors: Steven E. Hall, Ewing Township, Mercer County; Martin F. Haslanger, Lambertville; Ravi K. Varma, Belle Mead, all of N.J.

[73] Assignee: E. R. Squibb & Sons, Inc., Princeton, N.J.

[21] Appl. No.: 667,200

[22] Filed: Nov. 1, 1984

[51] Int. Cl.[4] .................. A61K 31/34; C07D 307/935
[52] U.S. Cl. .................................... 514/469; 549/463
[58] Field of Search ........................ 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off.
2039909 8/1980 United Kingdom.

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted prostaglandin analogs are provided having the structural formula

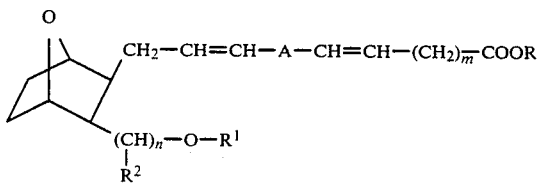

and including all stereoisomers thereof.

The compounds are cardiovascular agents useful, for example, in the treatment of thrombotic disease.

11 Claims, No Drawings

7-OXABICYCLOHEPTANE SUBSTITUTED OXA PROSTAGLANDIN ANALOGS AND THEIR ANTI-THROMBOTIC COMPOSITIONS AND METHODS

DESCRIPTION OF THE INVENTION

The present invention relates to 7-oxabicycloheptane substituted oxa prostaglandin analogs which are cardiovascular agents useful, for example, in the treatment of thrombotic disease. These compounds have the structural formula

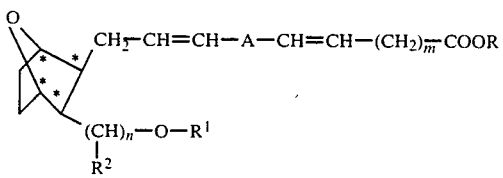

and including all stereoisomers thereof, wherein

A is a single bond or —$CH_2$—; m is 0 when A is $CH_2$ and m is 1 when A is a single bond; R is H, lower alkyl or alkali metal; n is 1 to 4; $R^1$ is lower alkyl, aryl, aralkyl, cycloalkyl or cycloalkylalkyl; and $R^2$ is H or lower alkyl.

Thus, the compounds of formula I of the invention encompass two basic types of compounds which have the following structures:

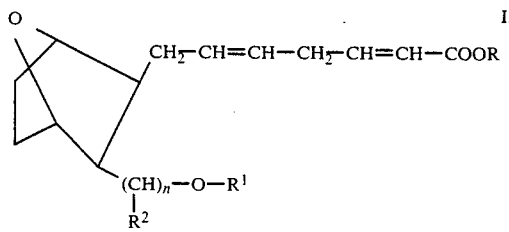

and

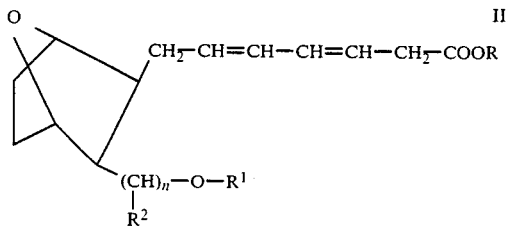

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" by itself or as part of another group includes any of the above lower alkyl, alkyl or aralkyl groups linked to an oxygen atom.

The term "halogen" or "halo" as used herein by itself or as part of another group refers to chlorine, bromine, fluorine or iodine with chlorine being preferred.

Preferred are those compounds of formula I wherein A is a single bond and m is 1 or A is $CH_2$ and m is 0, n is 1, R is H, $R^1$ is lower alkyl, aryl, such as phenyl, or aralkyl such as benzyl and $R^2$ is H.

The various compounds of the invention may be prepared as outlined below.

The compounds of formula I of the invention may be prepared as described below.

The starting ethers V or IX may be prepared according to the following reaction sequence.

A. Where n is 1

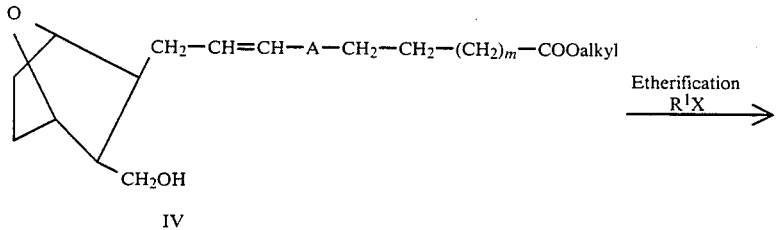

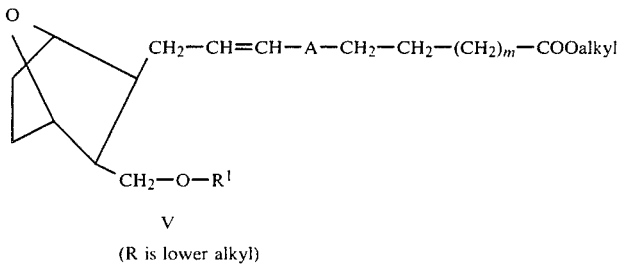
(R is lower alkyl)
B. Where n is 2 to 4
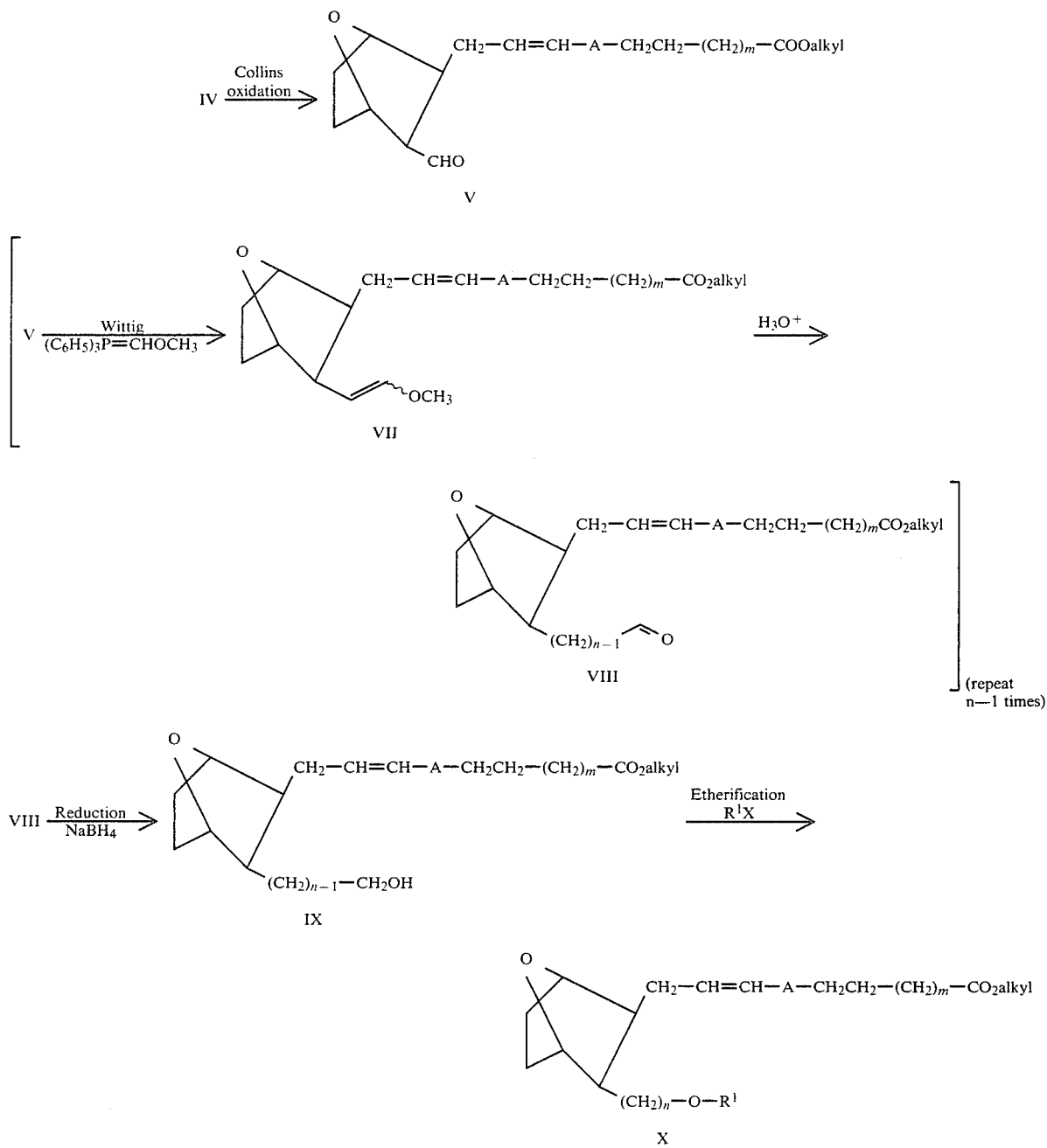
In the reaction sequence identified as "A", where in Formula I n is 1, the lower alkyl ester containing the hydroxymethyl group, that is, compound IV (prepared as described in U.S. Pat. No. 4,143,054) is employed as the starting material. Thus, compound IV is subjected to an etherification reaction, for example, by reacting a compound of the structure.

R¹X      A (wherein X is Cl, Br, I, OSO₂CH₃ or

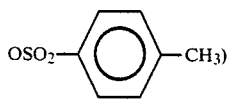

in the presence of a strong inorganic base such as KOH or NaOH, and an appropriate solvent to form ester V. In carrying out the above reaction, the hydroxymethyl compound IV is employed in a molar ratio to the halide A, that is, IV:A of within the range of from about 0.8:1 to about 1:5, employing a solvent such as xylene, tetrahydrofuran (THF), dimethylsulfoxide (DMSO) or dimethylformamide (DMF).

Where in R¹X, X is Br or Cl, a phase transfer etherification is employed in which case THF is used as the solvent and a phase transfer reagent such as Bu₄NHSO₄, or (C₆H₅CH₂)(CH₃)₃NHSO₄ is employed.

The starting alcohol IV wherein R² is lower alkyl may be prepared by reacting the aldehyde B

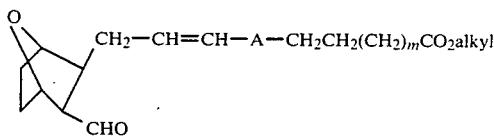

prepared as described in U.S. Pat. No. 4,143,054 with an alkyl Mg halide C of the structure R²MgX      C (wherein X is Cl or Br) at reduced temperatures of less than about 0° C. in the presence of an inert organic solvent such as tetrahydrofuran.

In the reaction sequence identified as "B", where in Formula I n is 2 to 4, the starting lower alkyl ester containing the hydroxymethyl group, that is, compound IV (prepared as described in U.S. Pat. No. 4,143,054) is used to form the aldehyde V. Thus, to form aldehyde V, compound IV is subjected to a Collins oxidation, for example, by reacting IV with chromium trioxide in pyridine.

The aldehyde V is used to prepare aldehyde VIII (where n is 2-4) by carrying out a homologation sequence, such as a Wittig reaction with (C₆H₅)₃P=CHOMe followed by hydrolysis, (n−1) times. The aldehyde VIII (where n is 2-4) is thus carried on to starting materials of this invention where n is 2-4, that is

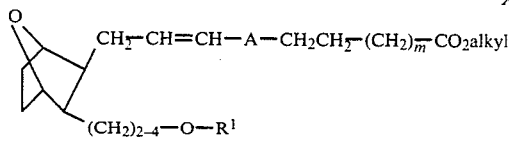

by reducing aldehyde VIII employing a reducing agent such as sodium borohydride or sodium cyanoborohydride in a solvent such as methanol to form the alcohol ester IX which is subjected to an etherification reaction as described above to form X.

Starting compounds of formula I wherein R¹ is aryl such as phenyl or substituted phenyl may be prepared by reacting the alcohol IV or X with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

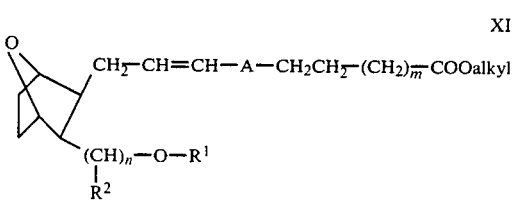

wherein R¹ is phenyl or substituted phenyl.

To prepare compounds of the invention, the ether V, X or XI is then subjected to phenylselenylation by reacting X with lithium diisopropylamide at reduced temperatures of from about −78° C. to about 0° C. in the presence of an inert organic solvent such as tetrahydrofuran, ether; thereafter a solution of diphenyl-diselenide in an inert organic solvent as described above is added and the reaction is maintained at reduced temperatures as described above to form the selenophenyl ester XII

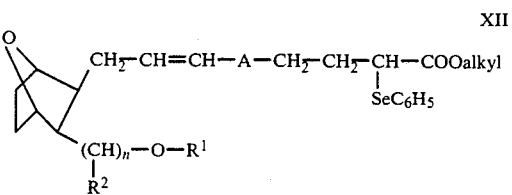

Where compounds of formula I of the invention wherein A is a single bond and m is 1 are desired, that is

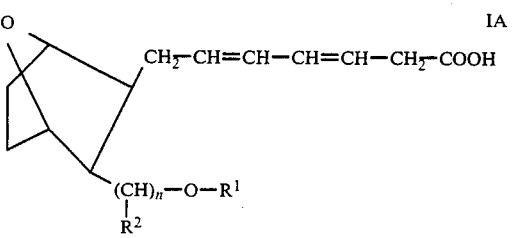

the selenophenyl ester XII where A is a single bond is made to undergo a selenoxide elimination reaction wherein the selenophenyl ester XI in a cooled alcohol solvent and/or ethyl acetate is reacted with hydrogen peroxide at reduced temperatures of from about 0° C. to about 25° C., to form the α,β-unsaturated ester XIII

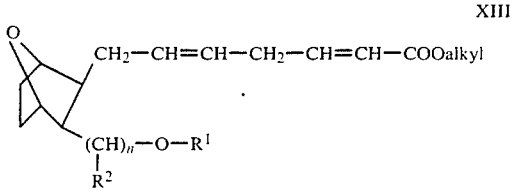

XIII

The ester XII is then hydrolyzed by treatment with a base such as lithium hydroxide, potassium carbonate or sodium hydroxide in the presence of an inert organic solvent such as tetrahydrofuran, methanol or dimethoxyethane-water to form the corresponding alkali metal salt which is then treated with strong acid such as HCl to form the acid compound of the invention IB

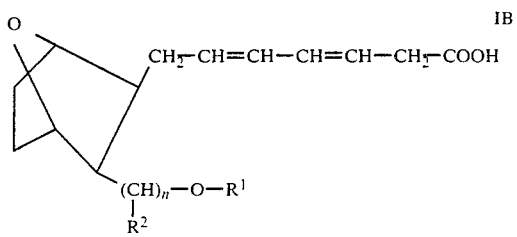

IB

Where compounds of formula I of the invention wherein A is $CH_2$ and m is 0 are desired, that is

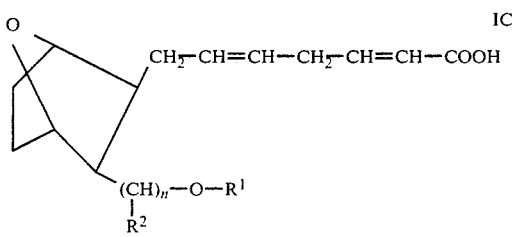

IC the selenophenyl ester XII is hydrolyzed by treatment with a base such as lithium hydroxide, potassium carbonate or sodium hydroxide in the presence of an inert organic solvent such as tetrahydrofuran, methanol or dimethoxyethane-water and then with a strong acid such as HCl to form the acid XIV

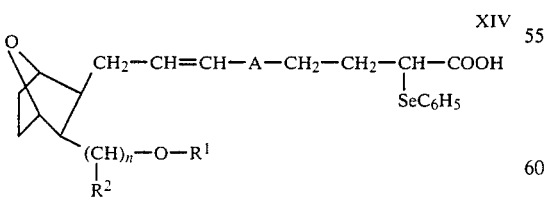

XIV

Acid XIV is then oxidized by reaction with hydrogen peroxide in the presence of an inert organic solvent such as tetrahydrofuran at reduced temperatures of from about 0° C. to about 25° C. to form the $\alpha,\beta$-unsaturated acid XV

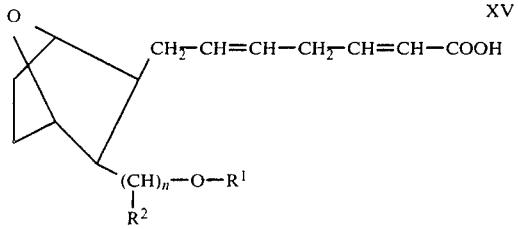

XV which is then hydrolyzed by treatment with strong acid such as HCl in the presence of an inert organic solvent such as dimethoxyethane-water to form acid IC.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

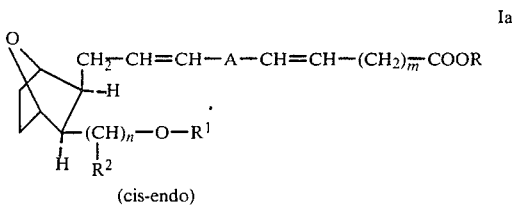

Ia (cis-endo)

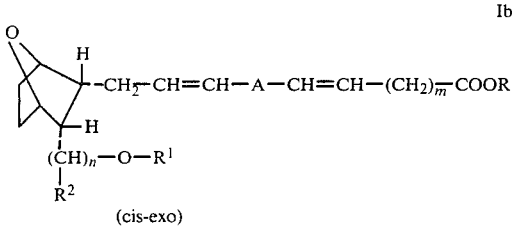

Ib (cis-exo)

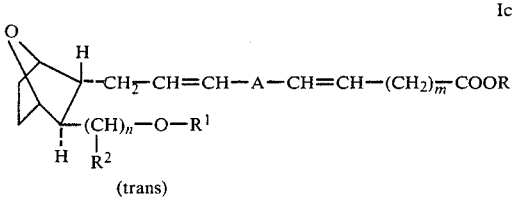

Ic (trans)

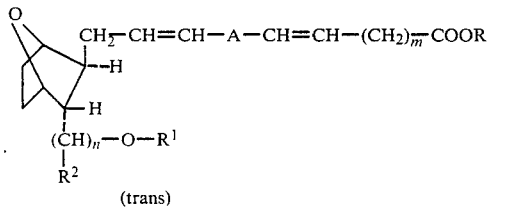

Id (trans)

The nucleus in each of the compounds of the invention is depicted as

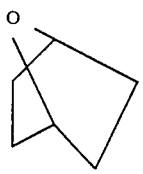

for matter of convenience; it will also be appreciated that the nucleus in the compounds of the invention may be depicted as

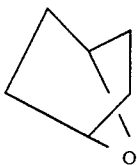

The compounds of this invention are cardiovascular agents useful as platelet aggregation inhibitors, such as in inhibiting arachidonic acid induced platelet aggregation, e.g., for treatment of thrombotic disease, such as inhibiting coronary or cerebral thromboses or in inhibiting bronchoconstriction, such as associated with asthma. The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention are also useful in combination with a cyclic AMP phosphodiesterase (PDE) inhibitor such as theophylline or papaverine in the preparation of and to prolong storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the invention. Unless otherwise indicated, all temperatures are expressed in degrees Centigrade.

EXAMPLE 1

[1R-[1α,2β(2E,5Z),3β,4α]]-7-[3-[(Hexyloxy)methyl]-7-oxabicyclo[2.2.1]hept-2-yl]-2,5-heptadienoic acid

A.

[1R-[1α,2β(Z),3β,4α]]-7-[3-[(Hexyloxy)-methyl]-7-oxabicyclo[2.2.1]hept-2-yl]-5-heptenoic acid, methyl ester (1) [3aR-[1-(1R,2S,5R),3aα,4α,7α,7aα]]-Octahydro-1-[[5-methyl-2-(1-methylethyl)-cyclohexyl]oxy]-4,7-epoxyisobenzofuran A solution of (exo)-octahydro-4,7-epoxyisobenzofuran-1-ol prepared as described in U.S. Pat. No. 4,143,054, (21 g, 0.13 mole), levomenthol (20.3 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,7aα]]-octahydro-1-[[5-methyl-2-(1-methylethyl)cyclohexyl]oxy]-4,7-epoxyisobenzofuran, m.p. 109°–111° C.

(2) [3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)-cyclohexyl]oxy]-4,7-epoxy-isobenzofuran (from Part (1)) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1) $R_f=0.25$; vanillin spray and heat.

(3) [3aS-(3aα,4α,7α,7aα)]-Octahydro-4,7-epoxyisobenzofuran-1-ol

A mixture of title (2) compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C. $[\alpha]_D= -44°$ $[\alpha]^{Hg}{}_{365}= -122°$ c=10 mg/ml MeOH TLC: silica gel; ethyl acetate/dichloromethane (1:1), $R_f=0.2$; vanillin spray and heat.

(4) [1R-(1α,2β,3β,4α)]-3-(Hydroxymethyl)-2-(2-methoxyethenyl)-7-oxabicyclo-[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane]

in tetrahydrofuran (20 ml). The mixture was stirred at room temperature for 30 minutes then treated with title (3) compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title product contaminated with phosphine oxide. This product was distilled in vacuo to yield 3 g of title compound, b.p. 90° C./0.01 mm. $[\alpha]_D = +44°$ $[\alpha]^{Hg}_{365} = +138°$ C. =11 mg/ml MeOH TLC: silica gel; ethyl acetate/dichloromethane (1:1); $R_f = 0.2$; vanillin spray and heat (5) [4aS-(4α,5α,8α,8aα)]-Octahydro-5,8-epoxy-(1H)-benzopyran-3-ol A solution of title (4) compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title compound, m.p. 104°–105° C.

$[\alpha]_D = -27.2°$ $[\alpha]^{Hg}_{365} = 0$ c=7.9 mg/ml MeOH (6) [1R-[1α,2β(Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title (5) compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$ $[\alpha]^{Hg}_{365} = 0$ c=16.9 mg/ml MeOH

TLC: silica gel; ether; $R_f = 0.4$; vanillin spray and heat.

(7) [1R-[1α,2β(Z),3β,4α]]-7-[3-[(Hexyloxy)methyl]-7-oxabicyclo[2.2.1]hept-2-yl]-5-heptenoic acid Dry xylene (80 ml) containing powdered KOH (2.0 g, 35 mmole) was distilled under stirring to remove ~40 ml of xylene. A solution of optically active alcohol from Part (6) (1.073 g, 4.0 mmole) in dry xylene (20 ml) was then added and the distillation was continued to remove another 20 ml of xylene. A solution of n-hexylmesylate (3.6 g, 20 mmole) in xylene (10 ml) was then added resulting in a moderately exothermic reaction. A jelly-like deposit soon started to appear. After 1.5 hours, the mixture was cooled, diluted with CH$_2$Cl$_2$ (100 ml) and water (100 ml) and was acidified to pH 2.0 with concentrated HCl. The CH$_2$Cl$_2$ layer was separated and the aqueous layer was extracted with CH$_2$Cl$_2$ (3×75 ml). The CH$_2$Cl$_2$ solutions were then combined, washed successively with small amounts of brine and water, dried (MgSO$_4$, anhydrous) and was evaporated to afford title acid as an oil contaminated mainly with impurities derived from n-hexylmesylate. A comparative tlc (silica gel, CH$_3$OH—CH$_2$Cl$_2$, 4:96) examination revealed that the n-hexylester or methylester of the title acid were absent in this mixture.

(8) [1R-[1α,2β(Z),3β,4α]]-7-[3-[(Hexyloxy)methyl]-7-oxabicyclo[2.2.1]hept-2-yl]-5-heptenoic acid, methyl ester 1.34 g (4 mmole) of the Part (7) acid was dissolved in Et$_2$O (~30 ml), and a moderate excess of a solution of diazomethane in Et$_2$O was added. After 5.0 minutes, the excess diazomethane was destroyed by the addition of 2-3 drops of glacial acetic acid. After evaporation of the solvent, the residue was flash-chromatographed on a column of silica gel (LP-1, 40 g) eluting the column with ether-hexane (15:85), with tlc monitoring of the fractions, to isolate slightly impure title methyl ester, (430 mg, 31%) and pure title methyl ester (958 mg, 68%)[1] as oils with consistent IR, H$^1$—NMR and C$^{13}$—NMR and $[a]_D^{25} + 5.47°$ (C, 2.01; CHCl$_3$). The total yield was 99%.

Anal Calcd for C$_{21}$H$_{36}$O$_4$: C, 71.55; H, 10.29. Found: C, 71.29; H, 10.37.

270 MHZ H$^1$—NMR spectrum (CDCl$_3$): δ0.9 (t, 3H, J=8.5, CH$_3$), 1.3 (s, 8 to 9H, CH$_2$), 2.03 (m, 5H, J=~9.0, CH$_2$CH=), 2.31 (t, 2H, J=8.5, CH$_2$COO), 3.33 (m, 4H, J=9.0, CH$_2$O), 4.66 (s, 3H, COOCH$_3$), 4.3 (dd, 2H, J=~5.0 (Δ=59), H$_9$ and H$_{12}$), 5.4 (m, 2H, J=~5.0, 14, H$_5$ and H$_6$).

1. The H$^1$—NMR spectrum showed the presence of 3.5 to 4% of the trans-double bond isomer.

B.
[1R-[1α,2β(Z),3β,4α]]-7-[3-[(Hexyloxy)methyl]-7-oxabicyclo[2.2.1]hept-2-yl]-2-phenylselenyl-5-heptenoic acid, methyl ester A solution of diisopropylamine (120.1 mg, 1.2 mmole) in dry THF (2.5 ml) was cooled and stirred in a bath at −78° (dry ice-acetone) under an atmosphere of nitrogen and 1.7M n-BuLi in hexane (1.1 mmole, 0.66 ml) was added in the course of one minute. After 10 minutes, a solution of Part A methyl ester (1.1 mmole, 352.6 mg) in dry THF (3.0 ml) was added in the course of 2.0 minutes. The light yellow solution was stirred for 20 minutes. A solution of diphenyl diselenide (1.5 mmole, 468 mg) in dry THF (2.0 ml) was then added dropwise in the course of 4.0 minutes. Initially, the deep yellow color of the selenide disappeared and subsequently persisted. After 20 minutes, the mixture was added into a 5% $NH_4Cl$ solution (30 ml) which was then extracted with $Et_2O$ (3×40 ml). The extracts were combined, washed with water (2×10 ml), dried ($MgSO_4$ anhydrous) and was evaporated to afford crude title α-selenophenyl ester as an oil. This was chromatographed on a column of silica gel (Baker, 60–200 mesh, 20 g) eluting the column with $Et_2O$ hexane (1:9, 1:4) to isolate homogeneous (tlc, $H^1$—NMR) title α-selenophenyl ester as an oil (402 mg, 79.3%) and the β-keto ester (70 mg, 10.4%) resulting from the self-condensation of the starting material (according to the $H^1$—NMR spectrum in $CDCl_3$). The title ester was an essentially 1:1 mixture of two C-2 distereomers on the basis of tlc (silica gel, 2:3, $Et_2O$-hexane, 2 developments). The C-2 proton appeared along with the COO $CH_3$ at 3.65δ as a triplet in the 270 MHz $H^1$—NMR spectrum ($CDCl_3$).

C.
[1R-[1α,2β(Z),3β,4α]]-7-[3-[(Hexyloxy)methyl]-7-oxabicyclo[2.2.1]hept-2-yl]-2-phenylselenyl-5-heptenoic acid A solution of Part B α-selenophenyl ester (402 mg, 0.792 mmole) in THF (10 ml) was stirred under an atmosphere of nitrogen with 1N LiOH (3.0 ml) for 20 hours. Then, concentrated HCl was added dropwise to pH~3.0. The mixture was then concentrated in vacuo, diluted with $H_2O$ (20 ml), saturated with salt and was extracted with $Et_2O$ (3×20 ml). The extracts were combined, washed with brine (2×10 ml), dried ($MgSO_4$ anhydrous) and was evaporated to afford title α-selenophenyl acid as an oil (402 mg, 100%) which was homogeneous by tlc ($R_f$= ~0.4; silica gel 1:9 ($H_3O-H-CHCl_3$).

D.
[1R-[1α,2β(2E,5Z),3β,4α]]-7-[3-[(Hexyloxy)methyl]-7-oxabicyclo[2.2.1]hept-2-yl]-2,5-heptadienoic acid A solution of Part C α-selenophenyl acid (402 mg, 0.81 mmol) in THF (9.0 ml) was stirred in an ice bath and 30% $H_2O_2$ (0.5 ml) was added. After a few minutes, the cold bath was removed and the stirring was continued at ambient temperature for 1 hour. The mixture was then diluted with $Et_2O$ (100 ml), washed with water (3×10 ml), dried ($MgSO_4$ anhydrous) and was evaporated to afford crude title acid as an oil. This was chromatographed on a column of silica gel (Baker, 60–200 mesh, 15.0 g) eluting the column with $Et_2O$-hexane (1:4 and 1:1) and $Et_2O$, with tlc monitoring of the fractions to isolate title acid as an oil (240 mg, 88%), $[\alpha]_D^{25}+14.55°$ (C, 1.72; $CHCl_3$) with consistent IR, $H^1$—NMR spectra and $C^{13}$ NMR spectra and MS data.

Anal Calcd for $C_{20}H_{32}O_4$ (MW 336.47): C, 71.39; H, 9.59. Found: C, 71.50; H, 9.67.

FX 270 $H^1$—NMR Spectrum ($CDCl_3$): δ ppm 0.90 (t, 3H, J=8.5, $H_{21}$), 7.3 (s, 2H, $CH_2$), 1.88 (t, 1H, J=8.5, --), 2.05 (sextet, 3H, J=~8.5,__), 2.98 (t, 2H, J=8.5, $H_4$), 3.35 (m, 4H, J=~8.5, $H_{14}+H_{16}$), 4.2 (d, 1H, J=~6.0, $H_{12}$), 4.4 (d, 1H, J=6.0, $H_9$), 5.47 (m, 2H, --, $H_5+H_6$), 5.85 (q, 1H, J=17.0, 2.0, $H_2$), 7.05 (ddd, 1H, J=~17.0, ~8.5, $H_3$), 10.4 (broad, 1H, COOH).

EXAMPLE 2

[1R-[1α,2β(5Z),3β,4α]]-7-[3-[(Hexyloxy)methyl]-7-oxabicyclo[2.2.1]hept-2-yl]-3,5-heptadienoic acid A.
[1R-[1α,2β(5Z),3β,4α]]-7-[3-[(Hexyloxy)methyl]-7-oxabicyclo[2.2.1]hept-2-yl]-3,5-heptadienoic acid, methyl ester A solution of [1R-[1α,2β(Z),3β,4α]-7-[3-[(hexyloxy)methyl]-7-oxabicyclo[2.2.1]hept-2-yl]-2-phenylselenyl-5-heptenoic acid, methyl ester prepared as described in Example 1 Part B (366 mg, 0.72 mmole) in a mixture of $CH_3OH$ (3.0 ml) and EtOAc (3.0 ml) was stirred in an ice bath and 30% hydrogen peroxide (0.5 ml) was added dropwise. After 10 minutes, the ice bath was removed and the solution was stirred at ambient temperature for 1.0 hour. It was then diluted with $Et_2O$ (75 ml), washed with dilute brine, dried ($MgSO_4$ anhydrous) and was evaporated to afford title methyl ester (340 mg) as an oil. This was chromatographed on a column of silica gel (20 g; Baker, 60–200 mesh) eluting the column with hexane and $Et_2O$-hexane (5:95 and 1:9) to isolate homogeneous (tlc) title methyl ester as an oil (216 mg, 61.6%) with a consistent $H^1$—NMR spectrum.

B.
[1R-[1α,2β(5Z),3β,4α]]-7-[3-[(Hexyloxy)methyl]-7-oxabicyclo[2.2.1]hept-2-yl]-3,5-heptadienoic acid A solution of Part A methyl ester (216 mg, 0.617 mmole) in distilled THF (3.0 ml) was stirred with 1N LiOH (1.5 ml) under an atmosphere of nitrogen for 20 hours. The mixture was then acidified with concentrated HCl, diluted with brine (50 ml) and was extracted with ether (3×25 ml). The extracts were combined, washed with brine, dried ($MgSO_4$ anhydrous) and was evaporated to afford the crude title compound as an oil (200 mg). This was chromatographed on a column of silica gel (15 g), eluting the column with $Et_2O$-hexane (5:95; 1:9, 1:4 and 1:1) to isolate title acid as an oil (180 mg, 87%), with consistent IR, $H^1$—NMR, $C^{13}$—NMR and MS data.

Anal Calcd for $C_{20}H_{32}O_4$ (MW 336.47): C, 71.39; H, 9.59. Found: C, 70.99; H, 9.57.

$H^1$—NMR Spectrum ($CDCl_3$, FX-270): δ 0.89 (t, 3H, J=8.0, $H_{21}$), 1.31 (s, $CH_2$), 2.07 (q, 2H, J=8.0, $H_7$), 3.22 (q, 2H, J=8.0, $H_2$), 3.39 (m, 4H, J=8.0, $H_{14}+H_{16}$), 4.22 (d, 1H, J=~4.0, $H_9$), 4.42 (d, 1H, J=~4.0, $H_{12}$), 5.29 to 6.5 (m, 4H, J=8.0, 12.0, $H_3+H_4+H_5+H_6$).

| $^{13}$C Spectra Data ($CDCl_3$) | |
|---|---|
| Carbon 1 | 176.60 |
| 2 | 37.80, 32.84 |
| 3,4,5,6 | 133.25, 131.10, 129.40, 128.78, 124.88, 126.63, 123.68, 121.95 |
| 7 | 26.25*, 29.35* (weak) |
| 8 | 46.90 |
| 9 | 79.40 |
| 10 | 29.60 |
| 11 | 29.54 |
| 12 | 79.99 |
| 13 | 46.37 |
| 14 | 71.31 |
| 15 | — |
| 16 | 69.86 |
| 17 | 26.14* |
| 18 | 25.83 |
| 19 | 31.64 |
| 20 | 22.57 |

-continued

| | ¹³C Spectra Data (CDCl₃) |
|---|---|
| 21 | 13.97 |

*Assignment is tentative

EXAMPLE 3

[1R-[1α,2β(5Z),3β,4α]]-7-[3-[(Heptyloxy)methyl]-7-oxabicyclo[2.2.1]hept-2-yl]-3,5-heptadienoic acid Following the procedure of Examples 1 and 2 except substituting n-heptylmethanesulfonate for n-hexylmethanesulfonate, the title compound is obtained.

EXAMPLE 4

[1R-[1α,2β(5Z),3β,4α]]-7-[3-[(Cyclohexyl)methyl]-7-oxabicyclo[2.2.1]hept-2-yl]-3,5-heptadienoic acid Following the procedure for Examples 1 and 2 except substituting cyclohexylmethanesulfonate for n-hexylmethanesulfonate, the title compound is obtained.

EXAMPLE 5

[1R-[1α,2β(5Z),3β,4α]]-7-[3-[(Propyloxy)methyl]-7-oxabicyclo[2.2.1]hept-2-yl]-3,5-heptadienoic acid Following the procedure of Examples 1 and 2 except substituting n-propylbromide for n-hexylmethanesulfonate, the title compound is obtained.

EXAMPLE 6

[1R-[1α,2β(2E,5Z),3β,4α]]-7-[3-[(Propyloxy)methyl]-7-oxabicyclo[2.2.1]hept-2-yl]-2,5-heptadienoic acid Following the procedure of Example 1 except substituting n-propylbromide for n-hexylmethanesulfonate, the title compound is obtained.

EXAMPLE 7

[1R-[1α,2β(2E,5Z),3β,4α]]-7-[3-[(Butyloxy)methyl]-7-oxabicyclo[2.2.1]hept-2-yl]-2,5-heptadienoic acid Following the procedure of Example 1 except substituting n-butylbromide for n-hexylmethanesulfonate, the title compound is obtained.

EXAMPLE 8

[1R-[1α,2β(2E,5Z),3β,4α]]-7-[3-[(Octyloxy)methyl]-7-oxabicyclo[2.2.1]hept-2-yl]-2,5-heptadienoic acid Following the procedure of Example 1 except substituting n-octyl methanesulfonate for n-hexylmethanesulfonate, the title compound is obtained.

EXAMPLE 9

[1R-[1α,2β(2E,5Z),3β,4α]]-7-[3-[(Phenyloxy)methyl]-7-oxabicyclo[2.2.1]hept-2-yl]-2,5-heptadienoic acid (a) Phenol (1 mmol) is added to a solution of triphenylphosphine (1 mmol), diethylazodicarboxylate (1 mmol) and the alcohol from Example 1 Part A (6) (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(5Z),3β,4α]-7-[3-[(phenyloxy)methyl]-7-oxabicyclo[2.2.1]hept-2-yl]-5-heptenoic acid, methyl ester.

(b) Following the procedure as set out in Example 1, the ester from part (a) is converted to the title compound.

EXAMPLE 10

[1R-[1α,2β(5Z),3β,4α]]-7-[3-[(Phenyloxy)methyl]-7-oxabicyclo[2.2.1]hept-2-yl]-3,5-heptadienoic acid (a) Phenol (1 mmol) is added to a solution of triphenylphosphine (1 mmol), diisopropylazodicarboxylate (1 mmol) and [1α,2β(Z),3β,4α]-7-[3(hydroxymethyl)-7-oxabicyclo[2.2.1]hept-2-yl]-5-heptenoic acid (prepared as described in U.S. Pat. No. 4,143,054) (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(Z),3β,4α]-7-[3-[(phenyloxy)methyl]-7-oxabicyclo[2.2.1]hept-2-yl]-5-heptenoic acid, methyl ester.

(b) Following the procedure as set out in Examples 1 and 2, the ester from part (a) is converted to the title compound.

EXAMPLE 11

[1R-[1α,2β(5Z),3β,4α]]-7-[3-[(Methyloxy)methyl]-7-oxabicyclo[2.2.1]hept-2-yl]-3,5-heptadienoic acid Following the procedure for Examples 1 and 2 except substituting methylbromide for n-hexylmethanesulfonate, the title compound is obtained.

EXAMPLE 12

[1R-[1α,2β(5Z),3β,4α]]-7-[3-[(Benzyloxy)methyl]-7-oxabicyclo[2.2.1]hept-2-yl]-3,5-heptadienoic acid Following the procedure of Examples 1 and 2 except substituting benzylbromide for n-hexylmethanesulfonate, the title compound is obtained.

EXAMPLE 13

[1R-[1α,2β(2E,5Z),3β,4α]]-7-[3-[(Benzyloxy)methyl]-7-oxabicyclo[2.2.1]hept-2-yl]-3,5-heptadienoic acid Following the procedure of Example 1 except substituting benzyl methanesulfonate for n-hexyl methanesulfonate, the title compound is obtained.

EXAMPLE 14

[1R-[1α,2β(5Z),3β,4α]]-7-[3-[(Cyclohexylmethyloxy)methyl]-7-oxabicyclo[2.2.1]hept-2-yl]-3,5-heptadienoic acid Following the procedure of Examples 1 and 2 except substituting cyclohexylmethyl methanesulfonate for n-hexyl methanesulfonate, the title compound is obtained.

EXAMPLE 15

[1R-[1α,2β(2E,5Z),3β,4α]]-7-[3-[(Cyclopentylethyloxy)methyl]-7-oxabicyclo[2.2.1]hept-2-yl]-2,5-heptadienoic acid Following the procedure of Example 1 except substituting cyclopentylethyl methanesulfonate for n-hexyl methanesulfonate, the title compound is obtained.

EXAMPLE 16

[1R-[1α,2β(5Z),3β,4α]]-7-[3-[2-(Hexyloxy)ethyl]-7-oxabicyclo[2.2.1]hept-2-yl]-3,5-heptadienoic acid

A.
[1β,2α(5Z),3α,4β]-7-[3-(2-Oxo)ethyl]-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P$^+$—$CH_2OCH_3Cl^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl]-7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B. [1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with NaBH$_4$ (0.19 g, 5 mmol) in an argon atmosphere at 0° C. After stirring at 0° C. for 1 hour, the reaction was quenched by addition of 2N HCl (to pH 2). The methanol was removed in vacuo and the reaction mixture was taken up in ether. The ether solution was washed with saturated KHCO$_3$, saturated NaCl and dried (MgSO$_4$). The ether was evaporated to yield the title B compound.

C.
[1R-[1α,2β(5Z),3β,4α]-7-[3-[2-(Hexyloxy)-ethyl]-7-oxabicyclo[2.2.1]hept-2-yl]-3,5-heptadienoic acid Following the procedure of Examples 1 and 2 except substituting the above part B alcohol for the alcohol used in Example 1, the title compound is obtained.

EXAMPLE 17

[1R-[1α,2β(5Z),3β,4α]]-7-[3-[(Phenyloxy)ethyl]-7-oxabicyclo[2.2.1]hept-2-yl]-3,5-heptadienoic acid Following the procedure of Example 10 except substituting [1β,2α(5Z),3α,4β]-7-[3-[2-(hydroxy)ethyl]-7-oxabicyclo[2.2.1]hept-2-yl]-5-heptenoic acid, methyl ester for [1β,2α(5Z),-3α,4β]-7-[3-(hydroxymethyl)-7-oxabicyclo[2.2.1]hept-2-yl]-5-heptenoic acid, methyl ester, the title compound is obtained.

EXAMPLE 18

[1R-[1α,2β(2E,5Z),3β,4α]]-7-[3-[2-(Phenyloxy)ethyl]-7-oxabicyclo[2.2.1]hept-2-yl]-2,5-heptadienoic acid Following the procedure of Example 9 except substituting [1β,2α(5Z),3α,4β]-7-[3-[2-(hydroxy)-ethyl]-7-oxabicyclo[2.2.1]hept-2-yl]-5-heptenoic acid, methyl ester for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 19

[1R-[1α,2β(5Z),3β,4α]]-7-[3-[2-(Benzyloxy)ethyl]-7-oxabicyclo[2.2.1]hept-2-yl]-3,5-heptadienoic acid Following the procedure of Examples 16, 1 and 2 except substituting benzyl methanesulfonate for n-hexyl methanesulfonate, the title compound is obtained.

EXAMPLE 20

[1R-[1α,2β(2E,5Z),3β,4α]]-7-[3-[2-(Benzyloxy)ethyl]-7-oxabicyclo[2.2.1]hept-2-yl]-2,5-heptadienoic acid Following the procedure of Examples 16 and 1 except substituting benzyl methanesulfonate for n-hexyl methanesulfonate, the title compound is obtained.

EXAMPLE 21

[1R-[1α,2β(5Z),3β,4α]]-7-[3-[2-(Cyclopentyloxy)ethyl]-7-oxabicyclo[2.2.1]hept-2-yl]-3,5-heptadienoic acid Following the procedure of Examples 16, 1 and 2 except substituting cyclopentyl methanesulfonate for n-hexyl methanesulfonate, the title compound is obtained.

EXAMPLE 22

[1R-[1α,2β(5Z),3β,4α]]-7-[3-[2-(Cyclohexyloxy)ethyl]-7-oxabicyclo[2.2.1]hepdt-2-yl]-3,5-heptadienoic acid Following the procedure of Examples 16, 1 and 2 except substituting cyclohexyl methanesulfonate for n-hexyl methanesulfonate, the title compound is obtained.

EXAMPLE 23

[1R-[1α,2β(5Z),3β,4α]]-7-[3-[4-(Hexyloxy)butyl]-7-oxabicyclo[2.2.1]hept-2-yl]-3,5-heptadienoic acid

A.
[1β,2α(5Z),3α,4β]-7-[3-(3-Oxo)propyl-7-oxabicyclo[2.2.1]hept-2-yl]-5-heptenoic acid, methyl ester Following the procedure of Example 16, part A except substituting [1β,2α(2Z),3α,4β]-7-[3-(2-oxo)-ethyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title A compound is obtained.

B.
[1β,2α(5Z),3α,4β]-7-[3-(4-Oxo)butyl-7-oxabicyclo[2.2.1]hept-2-yl]-5-heptenoic acid, methyl ester Following the procedure of Example 16, part A, except substituting the aldehyde from part A above, for [1β,2α(5Z),3α,4β]-7-[3-formyl-7-oxabicyclo-[2.2.1]hept-2-yl]-5-heptenoic acid, methyl ester, the title B aldehyde is obtained.

C.
[1β,2α(5Z),3α,4β]-7-[3-(4-Hydroxybutyl)-7-oxabicyclo[2.2.1]hept-2-yl]-5-heptenoic acid, methyl ester Following the procedure of Example 16, part B, except substituting the title B aldehyde for [1β,2α(5Z)-,3α,4β]-7-[3-(2-oxo)ethyl-7-oxabicyclo[2.2.1]hept-2-yl]-5-heptenoic acid, methyl ester, the title C alcohol is obtained.

D.
[1β,2α(5Z),3α,4β]-7-[3-[4-(Hexyloxy)-butyl]-7-oxabicyclo[2.2.1]hept-2-yl]-3,5-heptadienoic acid Following the procedure of Examples 1 and 2. except substituting the above part C alcohol for the alcohol used in Example 1, the title compound is obtained.

EXAMPLE 24
[1R-[1α,2β(2E,5Z),3α,4β]]-7-[3-[4-(Cyclohexyloxy)-butyl]-7-oxab icyclo[2.2.1]hept-2-yl]-2,5-heptadienoic acid Following the procedure of Examples 23 and 1 except substituting cyclohexyl methanesulfonate for n-hexyl methanesulfonate, the title compound is obtained.

EXAMPLE 25
[1R-[1α,2β(5Z),3β,4α]]-7-[3-[4-(Phenyloxy)butyl]-7-oxabicyclo[2.2.1]hept-2-yl]-3,5-heptadienoic acid Following the procedure of Examples 10, 1 and 2 except substituting [1β,2α(5Z),3α,4β]-7-[3-(4-hydroxybutyl)-7-oxabicyclo[2.2.1]hept-2-yl]-5-heptenoic acid, methyl ester for [1β,2α(5Z),3α,4β]-7-[3-(hydroxymethyl)-7-oxabicyclo[2.2.1]hept-2-yl]-5-heptenoic acid, methyl ester, the title compound is obtained.

EXAMPLE 26
[1R-[1α,2β(2E,5Z),3β,4α]]-7-[3-[4-(Benzyloxy)butyl]-7-oxabicyclo[2.2.1]hept-2-yl]-2,5-heptadienoic acid Following the procedure of Examples 23 and 1 except substituting benzyl methanesulfonate for n-hexyl methanesulfonate, the title compound is obtained.

What is claimed is:

1. A compound having the structural formula

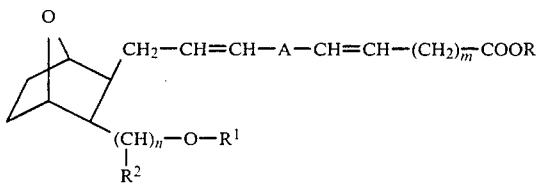

and including all stereoisomers thereof;
wherein A is a single bond or —CH$_2$—; m is 0 when A is —CH$_2$— and m is 1 when A is a single bond; R is H, lower alkyl or alkali methyl; R$^1$ is lower alkyl, aryl, aralkyl, cycloalkyl or cycloalkylalkyl; n is 1 to 4; and R$^2$ is H or lower alkyl, wherein the term lower alkyl or alkyl by itself or as part of another group contains 1 to 12 carbons and is unsubstituted or substituted with halo, trifluoromethyl, aryl, alkoxy, haloaryl, alkyl-aryl, cycloalkyl or alkylcycloalkyl;

the term aryl by itself or as part of another group contains 6 to 10 carbons and is unsubstituted or substituted with 1 or 2 lower alkyl groups, 1 or 2 halogens and/or 1 or 2 lower alkyl groups;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups.

2. The compound as defined in claim 1 wherein A is a single bond and m is 1.

3. The compound as defined in claim 1 wherein A is —CH$_2$— and m is 0.

4. The compound as defined in claim 1 wherein R$^2$ is H and n is 1.

5. The compound as defined in claim 4 wherein R$^1$ is butyl, pentyl, hexyl, heptyl or 1,1-dimethylpentyl.

6. The compound as defined in claim 1 having the name [1R-[1α,2β(2E,5Z),3β,4α]]-7-[3-[(hexyloxy)methyl]-7-oxabicyclo[2.2.1]hept-2-yl]-2,5-heptadienoic acid, including all stereoisomers thereof.

7. The compound as defined in claim 1 having the name [1R-[1α,2β(5Z),3β,4α]]-7-[3-[(hexyloxy)methyl]-7-oxabicyclo[2.2.1]hept-2-yl]-3,5-heptadienoic acid including all stereoisomers thereof.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

11. A method of inhibiting bronochoconstriction associated with asthma, inhibiting platelet aggregation and bronchoconstriction by inhibiting production of thromboxane A$_2$ by blocking the action of thromboxane synthetase, treating inflammation or relieving pain which comprises administering to a mammalian host an effective amount of a compound as defined in claim 1 or a pharmaceutically acceptable salt thereof.

* * * * *